United States Patent [19]

Magyar et al.

[11] Patent Number: 5,589,513

[45] Date of Patent: Dec. 31, 1996

[54] PHARMACEUTICAL COMPOSITION AND PROCESS FOR THE PREPARATION THEREOF

[75] Inventors: Kálmán Magyar; József Gaál; István Sziráki; József Lengyel; Anna Z. Szabó, all of Budapest; Katalin Mármarosi, Biatorbágy; István Hermecz, Budapest; István Szatmári, Budapest; Zoltán Török, Budapest; Péter Körmöczy, Budapest, all of Hungary

[73] Assignee: Chinoin Gyogyszer es Vegyeszeti Termekek Gyara Rt., Budapest, Hungary

[21] Appl. No.: 256,128

[22] PCT Filed: Dec. 18, 1992

[86] PCT No.: PCT/HU92/00060

§ 371 Date: Jun. 17, 1994

§ 102(e) Date: Jun. 17, 1994

[87] PCT Pub. No.: WO93/12775

PCT Pub. Date: Jul. 8, 1993

[30] Foreign Application Priority Data

Dec. 20, 1991 [HU] Hungary .................. 4060/91

[51] Int. Cl.$^6$ .................. A01N 33/02; A61K 31/135
[52] U.S. Cl. .................. 514/654
[58] Field of Search .................. 514/654

[56] References Cited

U.S. PATENT DOCUMENTS

| | | | |
|---|---|---|---|
| 5,326,770 | 7/1994 | Wilkerson | 514/654 UX |
| 5,380,761 | 1/1995 | Szabo et al. | |
| 5,444,095 | 8/1995 | Tatton et al. | 514/654 |
| 5,508,311 | 4/1996 | Yu et al. | 514/654 UX |

*Primary Examiner*—Paul F. Shaver
*Attorney, Agent, or Firm*—Herbert Dubno; Jonathan Myers

[57] ABSTRACT

The invention relates to two phase pharmaceutical compositions comprising as active ingredient a MAO inhibitor and an uptake inhibitor together with usual pharmaceutical auxiliaries. The compositions can be used for the treatment of neurodegenerative diseases. As active ingredient optionally N-(1-phenyl-isopropyl)-N-methyl-propinylamine or N-(4-fluoro-phenyl)-isoprop-1-yl-N-methyl-propinylamine or their salts, optically active isomers or metabolites are used both as MAO inhibitor and as uptake inhibitor.

3 Claims, 5 Drawing Sheets

The level of the deprenyl in different brian area 45" after the 1.5 mg/kg oral treatment, calculated on the basis of $^3H$ and $^{14}C$ measurement The level of the CH-125 in different brain area 45" min after the 10mg/kg oral treatment calculated on the basis of $^3$H and $^{14}$C measurement

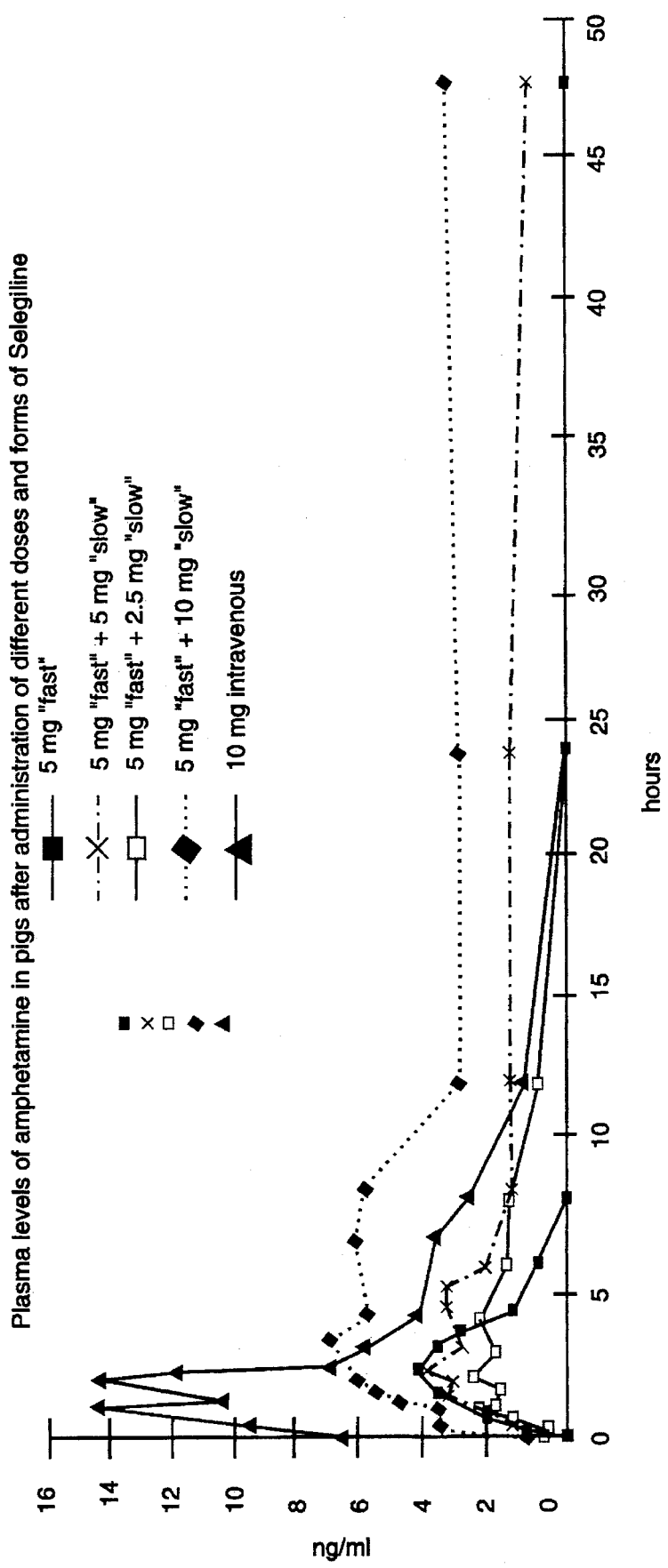

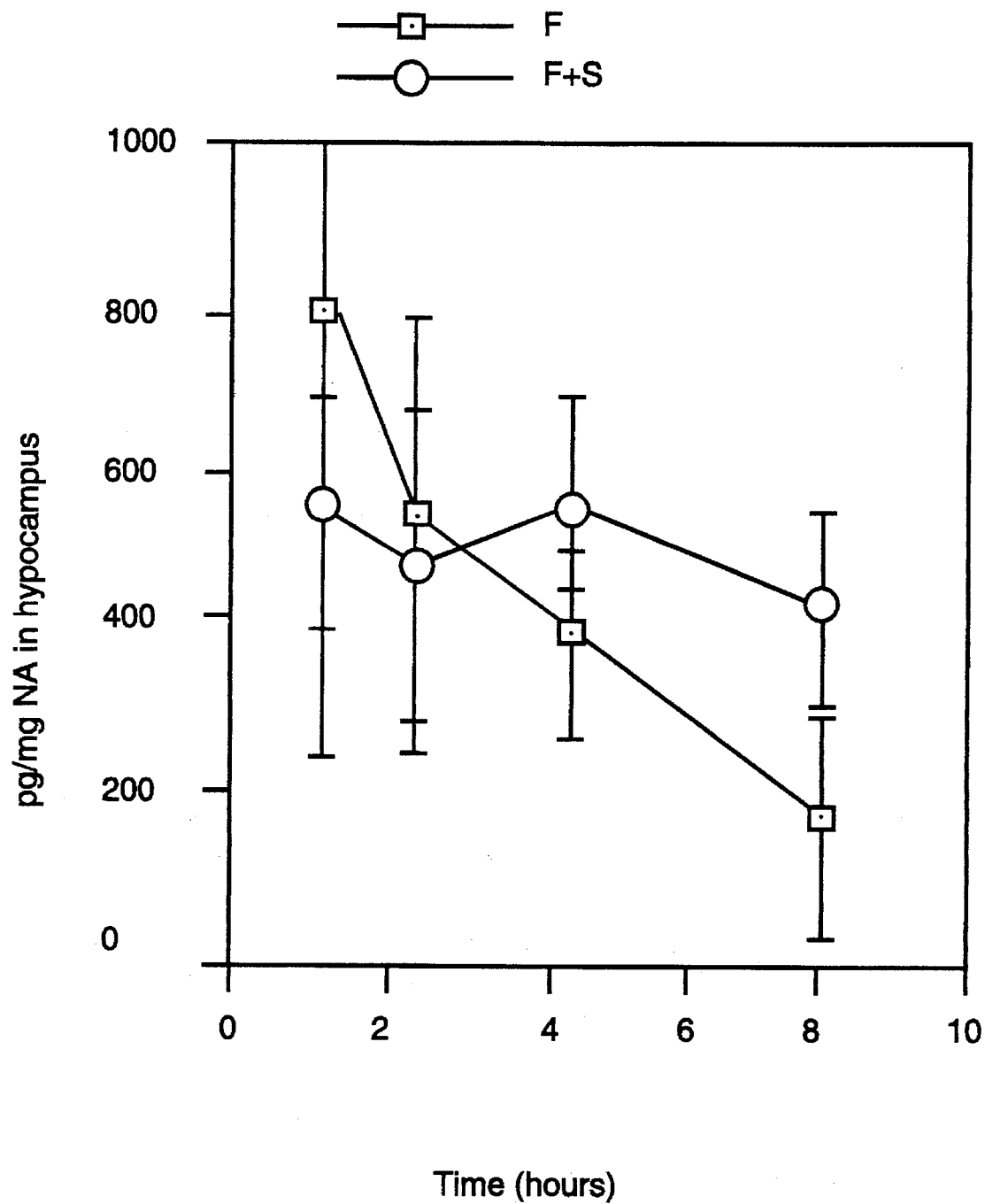

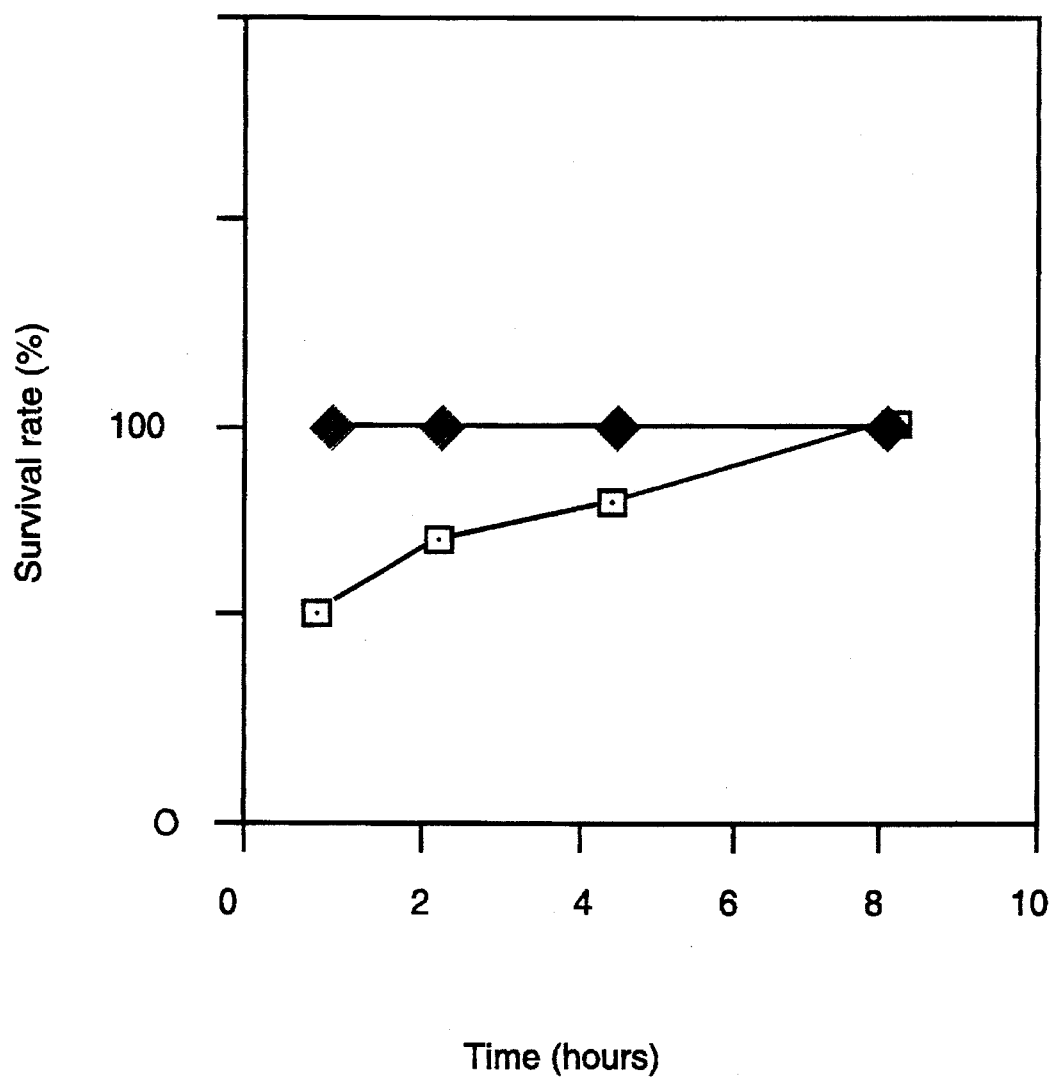

200
PHARMACEUTICAL COMPOSITION AND PROCESS FOR THE PREPARATION THEREOF

SPECIFICATION

This is a 371 of PCT/Hu92/08060, filed 12/18/92.

FIELD OF THE INVENTION

The invention relates to a pharmaceutical composition, suitable for the treatment of neurodegenerative diseases, containing active ingredients, resulting in adequate medicinal concentrations in time and level, both in the blood and the brain, and to a process for the preparation thereof.

BACKGROUND OF THE INVENTION

It is known, that monoamine oxidase (MAO) is one of the main metabolizing enzyme [Blaschko H. Pharmacol. Rev. 4, 415, (1951)] of biogenic amines occurring in the human nerve cells. Due to its activity the biogenic amines, playing an essential role in neurotransmission, are decomposed into ineffective metabolites. It was recognized that in certain diseases the level of the brain biogenic amines was decreased.

Agents, which inhibit the metabolizing enzyme (enzymes) can restore the normal level of these amines. This is the reason why MAO inhibitors were introduced in the human therapy. There are observations that MAO-inhibitions may lead to a serious side effect which is connected to tyramine (structurally a biogenic amine) potentiation ("cheese reaction") which is derived from foods and may induce blood pressure increase, and can be lethal. [Piackar and co-workers, Psychopharmacology 73, 3087, (1981)].

MAO exists in two forms, termed MAO-A and MAO-B. Inhibiting the B form selectively, the A form is able to decompose tyramine, which is a mixed type of substrate and the dangerous side effect can be avoided. This selective MAO inhibition can be accomplished by administration of (−)-deprenyl, [(−)N-(-1-phenyl-isopropyl)-N-methyl-propinylamine-hydrochloride)] which selectively and irreversibly inhibits the MAO-B enzyme [Elsworth et al., Psychopharmacology 57, 33, (1978)]. Because of the irreversible inhibition, the recovery of the enzyme activity can only be due to new enzyme resynthesis.

The development of the irreversible inhibition of the enzyme involves two steps. The first one is reversible and only the formation of the second enzyme-inhibitor complex becomes irreversible. The half life of enzyme regeneration is 7–8 days. [Oreland et al., J. Neural. Transm. Suppl. 32, 55–59 (1990)].

The substrate specificities of the enzymes and the selectivity of the mostly known inhibitors are reviewed by Dostert and his co-workers. [Medicinal Research Reviews, Vol 9, No. 1. 45–89, (1989)].

Balard [Science 219, 979–980, (1980)] and Burns (Proc. Natl. Acad. Sci 80, 4546–4550 (1983)] described that MPTP (1-methyl-4-phenyl-1,2,3,6-tetrahydropyridine) due to its neurotoxic activity evokes parkinsonian syndrome in man and similar symptoms can be observed in animal experiments. The MPTP causes selective damage of the dopaminergic neurons to the corpus striatum. The histological alterations are similar to those, observed in postmortem parkinsonian brains. It is known, that this effect of MPTP can be prevented with MAO inhibitors, especially with deprenyl. The preventing role of (−)-deprenyl is due to the inhibition of the conversion of MPTP to $MPP^+$, [Nature, 311, 467, (1984)]. The MPTP induced neuronal damage can be retarded also with dopamine uptake inhibitors [Proc. Natl. Acad. Sci. USA, 82, 2175, 1985] like mazindol, by inhibiting the active uptake of $MPP^+$ (methyl-phenyl-pyridinium ion) into the dopaminergic neurons.

During the period of MAO activity hydrogen peroxide and oxygen free radicals are formed, which can lead to oxydative damage of the neurons. Ammonia and some heterocyclic isoquinolines can also be formed by the MAO which can be considered neurotoxic. [Maret et al., Drug metabolism. Reviews, 22, 291–332, (1990); P. Riederer et al., Acta Neurol. Scand. 126, 41 (1989); Benedetti and Dostert, Biochem. Pharm. Vol 38, 555, (1989)].

It is known that DSP-4 [N-(2-chloroethyl)-N-ethyl-2-bromo-benzylamine], a neurotoxic agent, induces noradrenaline (NA) depletion selectively from the central and peripheral noradrenergic neurons [Grzanna et al., J. Histochem. Cytochem., 1435–1442, (1989)].

It is further known that—reuptake inhibitors such as desipramine [10,11-Dihydro-N-methyl-5-H-dibenz(6,7)azepine-5-propanamine) inhibit the NA-depleting effect of DSP-4 [Johnsson et al., Neuroscience, 7, 2895, (1982); Ross Br. J. Pharmacol., 58, 521, (1976)]—MDL 72974A [(E)-4-fluoro-beta-fluoro-ethylene benzene butamine] a highly selective MAO-B inhibitor lacks catecholaminergic reuptake blocking properties and fails to prevent DSP-4 induced toxicity [Finnegen et al. Eru. J. of Pharmacol., 184, 119–126 (1990)].

It became clear, that (−)-deprenyl cannot be considered only as a simple selective, irreversible inhibitor of MAO-B. It was stated, that it inhibits the uptake of dopamine, noradrenaline and tyramine in the nerve terminals and into the peripheral ganglions, but only in extremely high doses [Knoll, Advances in Biochem. Psychopharmacology Vol, 5, 393,(1972)]. It must be kept in mind that, in addition to the MAO inhibitory effect deprenyl possesses an uptake inhibitory activity.

The object of the invention is to prepare a pharmaceutical composition with optimal properties for the treatment of neurodegenerative diseases.

SUMMARY OF THE INVENTION

In the course of our experiments we learned that

1.) Longlasting MAO inhibition can be achieved only when the concentration of the inhibitor in the brain and blood reaches a sufficiently high (15–40 pmol/mg tissue) concentration. When the concentration of the inhibitor is too high (30 mg/die) the concentration of the metabolites will also be high enough to cause an undesired psychostimulant effect and/or the selectivity of the inhibitor will also be lost (MAO-A is also inhibited).

2.) Deprenyl and p-fluoro-deprenyl [N-(4-fluoro-phenyl)-isoprop-1-yl]-N-methyl-propinyl-amine exert their activity both as the parent (unchanged) compound and as the metabolites.

The results are illustrated in FIGS. 1 and 2.

After oral administration of alternatively and positionally labelled deprenyl and p-fluoro-deprenyl (ring-$^3$H and prop-argyl-$^{14}$C (1.5, 10 mg/kg, respectively) the distribution of the compounds were tested in 15 brain regions (the paired brain parts were separtely studied all together in 25 brain areas and in the plasma during 96 h, as a function of time in rats. It was stated, that the unchanged compound was quickly absorbed (15 minutes), and penetrated into the central nervous system. The unchanged deprenyl molecule has a short residence time in the brain, but the metabolites can be found for a longer period, in the tissues.

The simultaneous presence and the equal quantities of the two labels indicate the unchanged molecule (the data relate to the molar concentrations calculated on the basis of the two labels). Because of the fast change observed in the injected $^3H/^{14}C$ ratio in the tissues, our experiments indicate a significant metabolite formation (amphetamine, methylamphetamine, p-fluoro-methylamphetamine and p-fluoro-amphetamine) and their presence in the brain.

3.) The potential metabolites of deprenyl and p-fluoro-deprenyl, (methylamphetamine, amphetamine and p-fluoro-methylamphetamine, p-fluoro-amphetamine, respectively) have a significant uptake inhibitory potency; they can prevent in vivo the MPTP neurotoxicity without the development of a high degree of MAO inhibition. The results are shown in tables 1, 2 and 3. The tests were carried out according to the method of Heikilla [Nature, 311, 467–469 (1984)].

4.) The potential metabolites of deprenyl and p-fluoro-deprenyl (methylamphetamine, amphetamine and p-fluoro-methylamphetamine, p-fluoro-amphetamine, respectively) are able to prevent in vivo in a dose of 1–5 mg/kg (i.p.) the DSP-4 induced neurotoxicity without the development of MAO inhibition.

The results are shown in Table 8.

The tests were carried out according to the method of Finnegan [Finnegan et al., Eur. J. Pharmacol., 184, 119–126, (1990)].

Using the metabolites in high concentration in vivo (10 mg/kg; i.p.) they potentiated the toxic effect of the DSP-4 which was indicated by the death of the animals.

5.) To prevent the neurotoxicity either a properly high concentration of the Unchanged compound for a shorter period (a concentration necessary to complete irreversible MAO-B inhibition) or because of the reversibility of the uptake inhibition, the longlasting presence of the metabolites are needed.

It was found that maximal effect can be reached when both conditions are fulfilled.

BRIEF DESCRIPTION OF THE DRAWINGS

FIG. 3 is a series of 5 graphs plotting the plasma level of amphetamine in pigs, expressed in ng/ml along the Y-axis, against time expressed in hours along the X-=axis. The amphetamine in the plasma in each case is a metabolite resulting from administration to the pig of Selegiline, which is (−)-deprenyl, either orally, intravenously, or orally in a two phase composition containing the drug in both fast release and slow release form in various proportions.

FIG. 4 is a series of 2 graphs plotting along the Y-axis the level of noradrenaline (NA) in the hippocampus of rats against time, expressed in hours along the X-axis. The rats in each case were orally administered 3 mg/kg of (−)-deprenyl. In one case the entire 3 mg/kg were administered as a "fast" composition, in the other case the 3 mg/kg were administered as 1 mg/kg "fast" and 2 mg/kg "slow". Following oral administration of (−)-deprenyl, by 1,2,4 or 8 hours, DSP-4 was administered to the rats, intraperitoneally, and the inhibition of DSP-4 neurotoxicity was comparatively determined in each case.

FIG. 5 is a series of two graphs plotting survival rate of rats as a percentage along the Y-axis, against time, expressed in hours along the X-axis. In each case the total amount of (−)-deprenyl orally administered is 4 mg/kg as either all "fast" composition or as 2 mg/kg "fast" and 2 mg/kg "slow". Once again DFP-4 was intraperitoneally administered to the rats after the (−)-deprenyl was administered.

Figure 1:
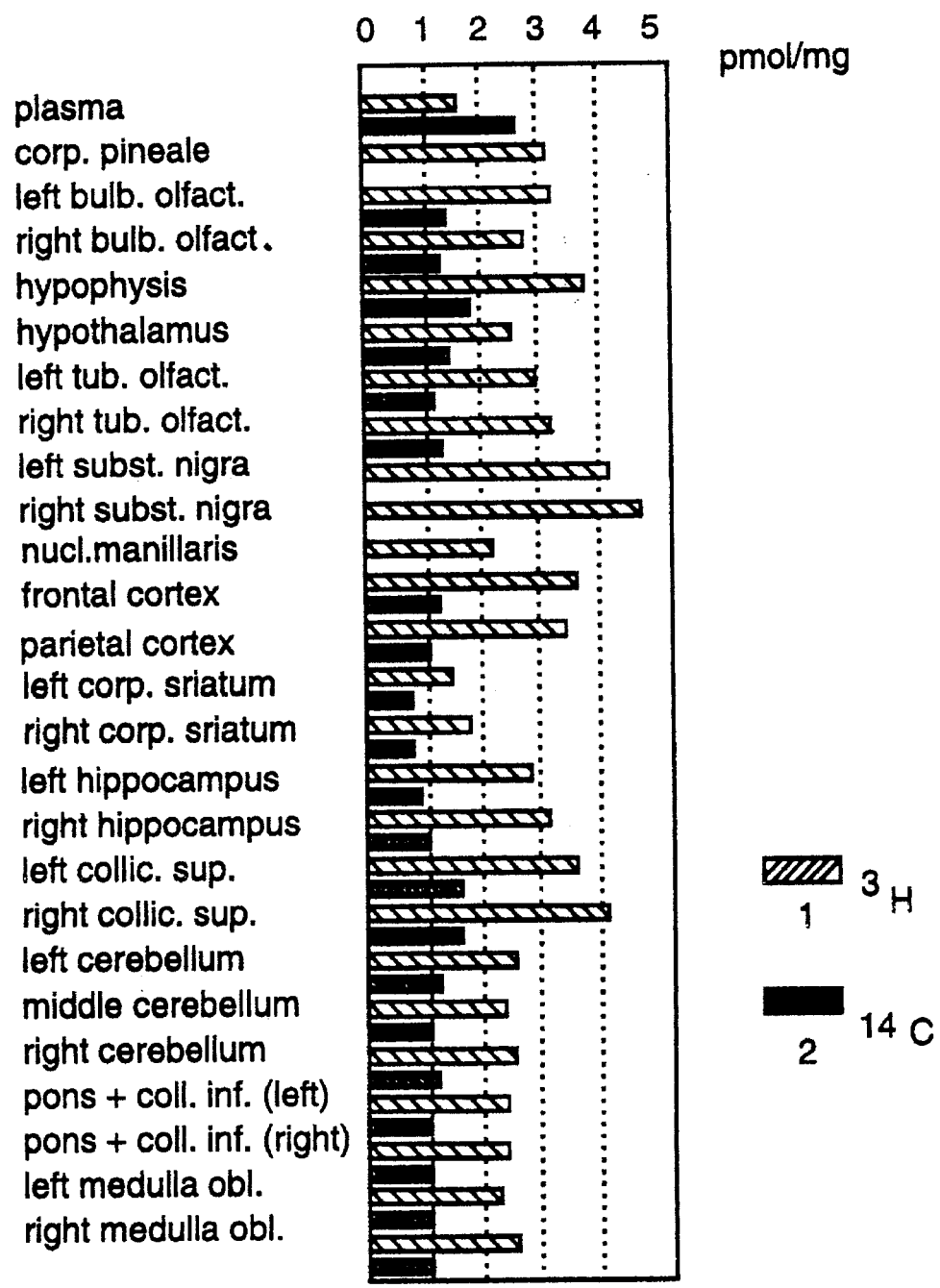
FIG. 1 is a bar graph showing the level of deprenyl labelled with $^3H$ on the phenyl moiety and $^{14}C$ on the propargyl moiety in 25 different areas of a rat brain 45 minutes after oral administration of the labelled deprenyl (1.5 mg/kg) to the rat based on measurement of the $^3H$ and $^{14}C$.
Figure 2:
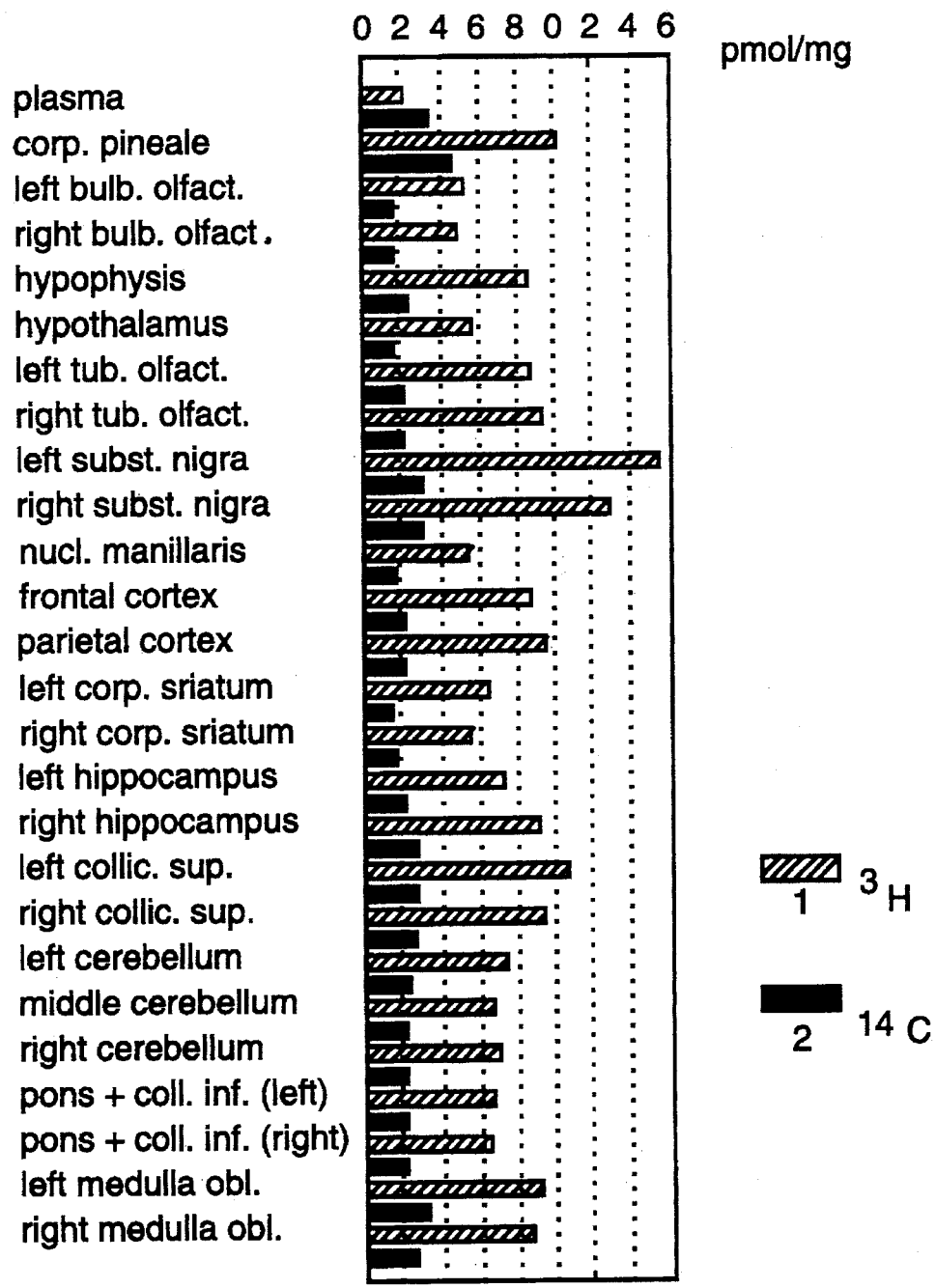
FIG. 2 is a bar graph showing the level of p-fluoro-deprenyl (CH-175) labelled with $^3H$ on the phenyl moiety and $^{14}C$ on the propargyl moiety in 25 different areas of a rat brain 45 minutes after oral administration of the labelled p-fluoro-deprenyl (10 mg/kg) to the rat based on measurement of the $^3H$ and $^{14}C$.

The invention relates to two phase pharmaceutical compositions comprising as active ingredient a compound with MAO inhibiting effect and a compound with uptake inhibiting effect together with usual auxiliary materials.

The compositions according to the invention contain as active ingredient 5–95 mass % of a reversible or irreversible MAO inhibitor, 5–95 mass % of an uptake inhibitor advantageously of sustained activity in a ratio of 1-19: :19-1, advantageously in a ratio of 1:1, 1:2 or 1.3.

The composition is administered depending on the state of the patient, on the seriousness of the clinical picture and on the individual sensitivity of the patient in a dose of 5–20, advantageously 10 mg/day.

If the uptake inhibitor is not of a sustained activity, the inhibitor is advantageously used in a retard form.

As MAO inhibitor advantageously deprenyl, p-fluoro-deprenyl, their salts, or optically active isomers respectively can be applied.

As uptake inhibitors advantageously deprenyl, p-fluoro-deprenyl or a compound of the formula I

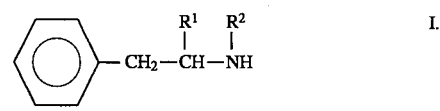

can be used, wherein $R^1$ is straight or branched $C_{1-8}$ alkyl, $C_{7-10}$ phenylalkyl, phenyl, $C_{3-8}$ cycloalkyl, $R^2$ is a straight or branched $C_{1-8}$ alkyl, a $C_{1-8}$ alkyl substituted by a halogen atom, by hydroxy-$C_{1-4}$ alkoxy or by one or two phenyls, phenyl or $C_{3-8}$ cycloalkyl with the proviso, that $R^1$ and $R^2$ contain together at least 3 carbon atoms—or an acid addition salt, or metabolite thereof.

As a compound of the formula I advantageously N-propyl-1-phenyl-2-pentylamine or its acid addition salt, N-propyl-1-phenyl-2-butylamine or its acid addition salt or N-propyl-1-phenyl-2-hexylamine or its acid addition salt can be used.

The two phase compositions according to the invention can be prepared by methods known per se in the form of pellets, tablets, coated tablets, transdermal compositions, dragee, suspension containing microcapsules, capsules, coated capsules, per os suspensions, suspension injections using known auxiliaries.

As auxuliaries advantageously the following materials can be used:

a.) As filling materials: saccharose, lactose, mannitol, starch, starch-talc-saccharose, calcium phosphate, hydroalcoholic solution of polyvidone (polyvinylpyrrolidone), etc. can be used.

b.) auxiliaries:

lypophilic base (stearic acid, stearic acid palmitate, glyceryl-ditripalmite-stearate, etc.);

Other auxiliaries known in the pharmaceutical technology: Eudragit derivatives, etc.

Cellulose-derivatives: HPMC, CMC, EC and their salts.

c.) Granulating liquid: water, ethanol, ethanol-water, isopropanol, isopropanol-water.

d.) Binders: PVP/VA, Eudragit derivatives, cellulose derivatives, and salts thereof.

One can proceed in a way too, that the pharmaceutical composition is prepared in situ, that is the patient is treated simultaneously with a suitable dose of MAO inhibitor needed to reach continuously a 98% MAO inhibition and a suitable dose of uptake inhibitor needed to reach a continuous uptake inhibition.

The preparation of deprenyl, p-fluoro-deprenyl, and compounds of the formula I is described in the U.S. Pat. No. 4,564,706; European patent specification No. 186,680 and Portuguese patent specification No. 85.799.

EXAMPLES

1.) A two phase tablet is prepared by a method known per se:

Composition
Internal phase: prepared by double granulation

| a.) | Deprenyl: | 5 mg |
| | Methocel k 4M premium: | 50 mg |
| | Lactose: | 20 mg |

Quantum satis of isopropanol for the preparation of granules.

| b.) | Deprenyl: | 10 mg |
| | Amylum maydis: | 40 mg |
| | Avicel PH-101: | 20 mg |
| | PVP K-25: | 10 mg |

Quantum satis of isopropanol for the preparation of granules (also distilled water can be used).

| External phase: | |
| --- | --- |
| Mg stearin: | 8 mg |
| Talcum: | 15 mg |
| Aerosil-200: | 2 mg. |

2.) Preparation of retard tablets containing 15 mg Deprenyl

| Component | |
| --- | --- |
| Deprenyl | 15 mg |
| Stearic acid | 30 mg |
| Eudragit RSPM | 45 mg |
| Collidon VA 64 | 47 mg |
| Carbopol 940 | 35 mg |
| Sterotex | 25 mg |
| Magnesium stearate | 3 mg |
| | 220 mg |

(Diameter of tablets 8 mm)

Technology of tabletting

1. Preparation of granules by dry granulating method well-known per se.

The sequence of powder-mixing: Collidon VA 64, Carbopol 940, Stearic acid, sterotex (atomized) (hydrogenated cottonseed oil), Eudragit RSPM (acrylic-methacrylic acid ester copolymer), Deprenyl.

2. Tabletting of powder mixture by eccentric tabletting machine at low r.p.m.

Results of dissolution test. Three parallel measurements were made. One cell contained 15 tablets.

a.) 316.5 cg/15 pieces
b.) 316.0 cg/15 pieces
c.) 319.0 cg/15 pieces

The medium used for dissolution was artificial gastric fluid without pepsin. (Ph. Hg. VII.)
Dilution is zero
d=1 cm
λ=256 mm

| | Results |
| --- | --- |
| Time (minute) | Dissolved active substance (%) |
| 10 | 4.5 |
| 15 | 9.0 |
| 30 | 21.0 |
| 60 | 31.2 |
| 90 | 47.7 |
| 120 | 39.3 |
| 150 | 41.1 |
| 180 | 48.6 |
| 240 | 51.9 |
| 300 | 63.3 |
| 360 | 69.0 |
| 420 (7 hours) | 75.6 |

3.) preparation of two phase pellets—"fast" and "slow" pellets with the following compositions are prepared.

| * FAST PELLETS | | |
| --- | --- | --- |
| - Neutral pellets (sugar spheres) | | 61.1 mg |
| - Deprenyl | | 16.3 mg |
| - Lactose | | 16.6 mg |
| - Polyvidone (K30) | | 6.3 mg |
| * SLOW PELLETS | | |
| - Neutral pellets (sugar spheres) | | 44.6 mg |
| - Deprenyl | | 11.9 mg |
| - Lactose | | 11.9 mg |
| - Polyvidone (K30) | | 4.6 mg |
| - Ethylcellulose | about | 8.4 mg |
| - Talc | about | 16.9 mg |
| - Castor oil | about | 1.7 mg |
| - manufacturing process | | |

Saccharose crystals are coated with a mixture of starch-saccharose and a hydroalcoholic solution of polyvidone and saccharose (sugar sphere).

A mixture of Deprenyl hydrochloride and lactose is attached on the microgranules using an alcoholic solution of polyvidone.

In the case of the "slow" pellet on the microgranules obtained an alcoholic varnish of ethylcellulose (plastified with Castor oil) and talc is applied.

To obtain the required "fast and slow" pellet the desired amounts of the "fast" and the "slow" pellets are mixed in a capsule by a method known per se.

4.) Preparation of two phase transdermal composition (UG-191)

| Components: | |
|---|---|
| Carbowax 35000 | 1.0 |
| Carbowax 4000 | 16.0 |
| Carbowax 400 | 53.0 |
| 1,2-propylene-glycol | 2.0 |
| Xanthan gum | 15.0 |
| Deprenyl | 7.0 |
| Cremophor EL | 6.0 |
| | 100.0 |

Technology

Carbowax components were fused and the mixture was poured into mixing vessel of Erweka type at 50° C. and was mixed on stage 6. Deprenyl was dissolved and suspended in a mixture of propylene glycol and Cremophor EL at 50° C. and the mixture in portions (50 g each) was added into the mixing vessel. After each portion the mixture was mixed 1 minute. Finally at increased speed (stage 9) Xanthan gum was added in portions (5 g each). After each portion the mixture was mixed 1 minute. Thereafter the speed of mixing was decreased to stage 3.5 and mixing was continued until cooling (appr. 1.5 hours). Content of active substance is 6.84% and stability is appropriate.

Liquid crystalline state: 100%, with translucent solid crystals of 8–10 microns. (Cremophor EL: glycerin-polyethylenglycol-ricinoleate. Xanthan gum: polysaccharide).

Pharmacological data

Planning the experimental conditions the following data have to be considered.

Direct in vivo measurement of the uptake inhibitory potency of the metabolites was not possible, because of their reversible nature.

The MAO-B inhibitor potency—using the platelet MAO-B activity as an indicator—peripherally is measurable in pigs (the platelets originated from other species do not contain good measurable MAO-B enzyme activity).

Measuring the time dependency of DSP-4 neurotoxicity in rats (using the noradrenaline content of hippocampus as an indicator) after pretreatment with different dosage forms of deprenyl the correlation between the lack of neurotoxicity of DSP-4 and the adequate but not extremely high blood level of the metabolites of deprenyl, can be demonstrated.

In a series of experiments the permanent level of deprenyl metabolites in the blood of the domestic pigs was measured with analytical techniques, and the platelet, brain and liver MAO activity was also determined.

The experiments were carried out on female (bit white) domestic pigs, weighing 20–25 kg. The pigs were caged separately during the experiments, and the same food was supplied, which was used formerly.

Animals were treated orally with 5; 7.5; 10; 15 mg of (−)-deprenyl in a pellet and with 10 mg iv. Blood samples (5 ml) were taken at 0; 0.08; 0.25; 0.5; 0.75; 1; 1.5; 2; 3; 4; 6; 12; 24 and 48 h in centrifuge tubes containing 500 IU heparin for analytical measurement. The samples were centrifuged at 1500 r.p.m. for 10 min. to separate plasma. The metabolites were determined by GC method, using Hp-5890 gas chromatograph, eluation time for methylamphetamine: 21.4 min.

The results are shown in FIG. 3.

The inhibition of DSP-4 neurotoxicity was measured in rats. For treating rats the schedule of Finnegan was followed [Finnegan et al., Eur. J. Pharmacol., 184, 119–126, (1990)].

Wistar male rats, weighing 170–200 g were used. Animals were housed six to a cage under constant temperature (22° C.), in a room illuminated 12 h per day. Food and water were freely available. Rats were pretreated orally with 3 mg/kg of the combination of example 3 (1 mg/kg "fast" (F)+2 mg/kg "slow" (S)), 1, 2, 4 and 8 hours before DSP-4 treatment (50 mg/kg; intraperitoneally).

Before the (−)-deprenyl pretreatment, the animals were starved for 24 h. Each hippocampus of the rats was by HPLC technique.

Results are shown in FIG. 4.

As it can be seen from FIG. 4, 3 mg/kg deprenyl p.o. can prevent the neurotoxicity of 50 mg/kg DSP-4 ip. in rats. In the case of the control ("fast") formulation this prevention is in the first period high (86.1%) but it decreases exponentially and after 8 hours reaches the level of DSP-4 treated control (19,6%). The claimed formulation produces 58.8% of inhibition, the inhibition is practically identical (54.5%) with that of the control formulation (51,5%) after two hours, but is significantly higher (43.31%) than that of those (16%) and does practically not change over eight hours. In the case of the treatment with 4 mg/kg deprenyl we found that the control ("fast") formulation was facilitated the neurotoxicity of DSP-4 time dependently in contrast to the claimed ("fast and slow") formulation. (See FIG. 5) This means that the dose of the "fast" component can not be increased unlimitedly without appearance of unwanted side effects.

Oppositely, applying the claimed compositions with increasing amounts of the "slow" part the inhibition of MAO-A will increase which means that the selectivity of deprenyl will be lost.

The results are given in Table 4.

TABLE 4

Percentage inhibition of MAO by deprenyl preparations

| Preparation | Brain | |
|---|---|---|
| | MAO-B | MAO-A |
| 1 mg/kg (tablets) | 88.02 ± 1.49 | 2.55 ± 0.56 |
| 0.5 ± 0.25 mg/kg ("fast" and "slow") | 85.84 ± 4.16 | 14.83 ± 3.37 |
| 0.5 ± 1.0 mg/kg ("fast" and "slow") | 90.50 ± 3.10 | 27.28 ± 3.93 |

Transdermal Tests on Pigs

In the case of transdermal preparations the control group was treated orally with 10 mg of (−)-deprenyl in a gelatinous capsule.

Blood samples were taken for the determination of MAO-B activity at: 0, 3, 6, 24, 48, 72 and 96 h. At 96 h after blood sampling the pigs were killed and the MAO-B and MAO-A activity were determined in their dissected brain.

The second group was treated as control with the UG-111 transdermal preparation containing 10 mg (−)-deprenyl. The times of blood sampling were at: 0, 3, 6, 24 and 48 h. The transdermal preparations were removed at 24 h. For the determinations of the residual (−)-deprenyl content of the preparations the patch and its nylon cover were used. The skin was washed with ethanolic cotton-wool, which was also used for HPLC determination. The pigs were killed at 48 h and MAO-A and MAO-B activity of the brain was determined.

The third group of the pigs was treated as control with UG-167 containing 20 mg of (−)-deprenyl. Blood samples were taken at: 0, 3, 6, 24, 48 and 72 h. The patches were removed at 48 h and the whole procedure described at group 2 was accomplished.

The fourth group of pigs was treated with UG-191 containing 30 mg of (−)-deprenyl. Blood samples were taken at: 0, 3, 6, 24, 48, 72 and 96 h. The patches were removed at 48 h and the whole procedure described at group 2 was accomplished.

The blood was taken from the v. cava cranialis with a 20 ml plastic syringe containing 1.5 ml of 7.6% Na-citrate solution. The volume of the blood taken was 18.5 ml at every sampling.

MAO activity was measured radiometrically according to the methods of Wurtman and Axelrod [Biochem. Pharmacol. 12. 1414–19; (1963)] with a slight modification [K. Magyar in: Monoamine Oxidases and their Selective Inhibition, Ed.: K. Magyar, Pergamon Press, Akadémiai Kiadó, Budapest, 11–21; (1980)].

The method described by Willberg and Oreland was followed for platelet preparation. (Med. Biol., 54: 137–44; 1976).

TABLE 5

Absorption of (−)-deprenyl form transdermal preparations as a function of time in pigs. (The residual (−)-deprenyl content of the patches was determined with HPLC technique).

| Transdermal preparation | Duration of experiment (h) | Remaining Deprenyl % + S.D. |
|---|---|---|
| UG-111 (control) 10 mg | 24 | 14.2 ± 5.5 |
| UG-167 (control) 20 mg | 24 | 36.5 ± 9.3 |
|  |  | 6.1 ± 5.1 |
| UG-191 20 mg | 24 | 58.5 ± 14.1 |
|  | 48 | 6.1 ± 5.1 |
|  | 72 | 8.4 ± 2.4 |

The results of the inhibition of MAO-B activity of the platelet after p. os and transdermal application are shown in Table 6.

TABLE 6

Effect of (−)-Deprenyl on the inhibition of MAO-B activity of the platelets (%) as compared to the control. Measurements vere made with $^{14}$C-PEA substrate. ±B.D. (n = 3)

| Mode of application | time |  |  |  |  |  |
|---|---|---|---|---|---|---|
|  | 3 | 6 | 24 | 48 | 72 | 96 |
|  | 97.77 | 86.04 | 100.00 | 82.67 | 72.32 | 0.0 |
|  | 92.52 | 96.51 | 100.00 | 70.48 | 65.63 | 0.0 |
| per os 1 | 0.0 | 95.63 | 100.00 | 69.93 | 50.17 | 0.0 |
| (10 mg) | 95.15 | 92.73 ± 3.35 | 100 ± 0.0 | 74.36 ± 4.16 | 52.71 ± 6.56 | — |
| UG-111 (control) | 0.0 | 36.27 | 52.68 | 60.70 | — | — |
| trans- 2 | 54.80 | 86.47 | 86.02 | 92.03 | — | — |
| dermal | 95.66 | 95.47 | 93.76 | 98.63 | — | — |
| (10 mg, 24 h) | 75.23 | 72.74 ± 18.42 | 77.49 ± 12.6 | 83.79 ± 11.7 | — | — |
| UG-167 (control) | 23.29 | 55.77 | 90.94 | 88.56 | 100.00 | — |
| trans- 2 | 72.11 | 95.90 | 98.54 | 91.44 | 89.34 | — |
| dermal | 65.81 | 65.05 | 0.0 | 90.57 | 75.02 | — |
| (20 mg, 48 h) | 53.74 ± 15.33 | 72.24 ± 12.13 | 94.74 | 90.19 ± 0.85 | 88.12 ± 7.24 | — |
| UG-191 | 85.76 | 90.55 | 98.18 | 94.02 | 95.08 | 96.52 |
| transderm. | 79.83 | 93.32 | 95.73 | 94.66 | 95.87 | 96.16 |
| (30 mg, 72 h) | 0.0 | 0.0 | 67.75 | 95.51 | 94.22 | 92.64 |
|  | 82.80 | 91.94 | 87.22 ± 9.76 | 94.73 ± 0.43 | 95.06 | 95.17 |

The results of the determination of MAO activity in the brain are shown in Table 7.

TABLE 7

Effect of (–)-Deprenyl on the inhibition of MAO activity (%) an compared to the control. Measurements were made in domestic pig brain nucleous free homogenates and in liver with $^{14}$C-PEA; $^{14}$C-5-HT substrate. ±B.S. (n = 3)

| Mode of application | | brain $^{14}$C-PEA | brain $^{14}$C-5-HT | liver $^{14}$C-PEA | liver $^{14}$C-5-HT |
|---|---|---|---|---|---|
| p. os | (96 h) | 73.22 ± 8.13 | 20.14 ± 6.0 | 41.04 ± 7.62 | 10.45 ± 6.4 |
| UG-111 transdermal | (48 h) (24 h) | 56.31 ± 10.03 | 16.39 ± 8.77 | 28.80 ± 5.15 | 13.7 0 0 |
| UG-167 transdermal | (72 h) (48 h) | 86.76 ± 6.67 86.76 ± 6.67 | 18.50 ± 3.81 18.50 ± 3.81 | 30.30 ± 10.23 30.30 ± 10.23 | 19.4 19.4 0 0 |
| UG-191 transdermal | (96 h) (72 h) | 88.82 ± 1.21 | 15.52 ± 3.35 | 16.92 ± 10.59 | 0 |

The composition, particle size, the precentage of liquid crystalline state of the different control preparations was as follows:

| UG-111 | |
|---|---|
| PEG 4000 | 16.0 g |
| PEG 400 | 60.0 g |
| Propyleneglycol | 8.0 g |
| Cremophor EL | 2.0 g |
| Deprenyl HCL | 5.0 g |
| PEG 400 ad | 100.0 g |

Average particle size: 72.7 microns; liquid crystalline state: 20%.

| UG-167 | |
|---|---|
| PEG 4000 | 19.0 g |
| PEG 400 | 55.0 g |
| Propyleneglycol | 8.0 g |
| Xanthan gum | 10.0 g |
| Deprenyl HCl | 5.0 g |
| PEG 400 ad | 100.0 g |

Average particle size: 91–109 microns; liquid crystalline state: 70–80%.

TABLE 1

IC$_{50}$ values of the Deprenyl and PFD metabolites on the MPP$^+$ uptake to the striatatal synaptosomes.

| Compound | IC$_{50}$ M | Compound | IC$_{50}$ M |
|---|---|---|---|
| (–)-deprenyl | — | (–)-p-F-deprenyl | — |
| (–)-desmethyl-deprenyl | — | (–)-p-F-desmethyl-deprenyl | — |
| (+)-desmethyl-deprenyl | 9.1 × 10$^{-6}$ | | |
| (–)-metamphetamine | 4.9 × 10$^{-7}$ | (–)-p-F-metamphetamine | 1.3 × 10$^{-6}$ |
| (+)-metamphetamine | 9.1 × 10$^{-8}$ | (+)-p-F-metamphetamine | 1.3 × 10$^{-6}$ |
| Homifensin | 3.1 × 10$^{-7}$ | (–)-p-F-amphetamine | 7.2 × 10$^{-7}$ |
| Mazindol | 1.7 × 10$^{-7}$ | (+)-p-F-amphetamine | 1.0 × 10$^{-7}$ |

TABLE 2

In vitro uptake inhibition on rat brain synaptosomas

| COMPOUND | NA HYPOTHALAMUS | DA STRIATUM | 5-HT HIPPOCAMPUS |
|---|---|---|---|
| (–)-DEPR. | 5.1 × 10$^{-5}$ | 1.0 × 10$^{-4}$ | 5.0 × 10$^{-3}$ |
| (+)-DEPR. | 1.7 × 10$^{-5}$ | 2.4 × 10$^{-5}$ | 3.6 × 10$^{-2}$ |
| (–)-p-FLUORO-D | 1.3 × 10$^{-5}$ | 2.9 × 10$^{-5}$ | 1.4 × 10$^{-3}$ |
| (+)-p-FLUORO-D | 6.1 × 10$^{-6}$ | 1.6 × 10$^{-5}$ | 6.0 × 10$^{-4}$ |
| (–)-METHYLAMPH. | 3.5 × 10$^{-6}$ | 4.2 × 10$^{-5}$ | — |
| (+)-METHYLAMPH. | 3.5 × 10$^{-7}$ | 6.0 × 10$^{-7}$ | 1.9 × 10$^{-2}$ |
| (–)-p-FLUORO-MA | 7.5 × 10$^{-6}$ | 3.0 × 10$^{-4}$ | — |
| (+)-p-FLUORO-MA | 7.7 × 10$^{-6}$ | 2.3 × 10$^{-5}$ | 1.7 × 10$^{-3}$ |

TABLE 3

The effect of deprenyl posttreatment on MPTP neurotoxicty

| 1. treatment | time beetwen treatments 30 | 2. treatment | Dopamine | % | DOPAC | % | MVA | % |
|---|---|---|---|---|---|---|---|---|
| physiological salt | | phys.s. | 15.1 ± 0.4 | 100 | 0.9 ± 0.02 | 100 | 1.4 ± 0.06 | 100 |
| MPTP | | " | 8.0 ± 0.5[a] | 53 | 0.7 ± 0.04[a] | 77 | 1.3 ± 0.07[a] | 79 |
| MPTP | | Deprenyl | 15.3 ± 0.4[b] | 101 | 0.9 ± 0.04[b] | 100 | 1.3 ± 0.05[c] | 93 |
| MPTP | | Pargyline | 7.1 ± 0.6[NS] | 47 | 0.5 ± 0.04[NS] | 55 | 0.9 ± 0.09[NS] | 64 |
| Pargyline | | MPTP | 13.8 ± 0.5[b] | 91 | 1.0 ± 0.06[b] | 111 | 1.4 ± 0.06[b] | 100 |
| MPTP | | Mazindol | 14.0 ± 0.8[b] | 98 | 1.1 ± 0.08[b] | 122 | 1.7 ± 0.10[b] | 121 |

[a]significantly lower than the control (p 0.01)
[b]significantly higher than group treated with MPTP (p. 0.01)
[c]significantly higher than group treated with MPTP (0.05 p 0.01)
[NS]no significant
DOPAC and HVA: metabolites of dopamine

TABLE 8

Interaction of (–)-deprenyl and (–)-p-fluoro-deprenyl metabolites with DSP-4 neurotoxicity in rats

| Pretreatment | | Treatment | Na content of hippocampus | |
|---|---|---|---|---|
| mg/kg; | i.p. | DSP-4 | in % ± S.D. | Survival % |
| (–)-MA | 1 | 50 | 61 ± 3.5 | 100 |
| (–)-MA | 5 | 30 | 116 ± 2.1 | 63 |
| (–)-MA | 10 | 50 | nd* | 0 |
| (–)-p-F-MA | 10 | 50 | nd* | 0 |

*nd: not determined. Because of the toxic interaction animals died within the first day.
MA = methylamphetamine
p-F-MA = p-fluoro-methylamphetamine.

What we claim is:

1. A pharmaceutical composition for treating a neurodegenerative disease by selectively inhibiting MAO-B activity without inhibiting MAO-A activity and by inhibiting uptake of a biogenic amine to the brain, which consists essentially of:

(a) a fast-acting MAO-B inhibitor in an amount effective to inhibit MAO-B selected from the group consisting of deprenyl and p-fluoro-deprenyl or a pharmaceutically acceptable acid addition salt thereof; and (b) a slow-acting inhibitor of uptake of a biogenic amine in an amount effective to inhibit uptake of a biogenic amine, said slow-acting inhibitor of uptake of a biogenic amine selected from the group consisting of deprenyl and p-fluoro-deprenyl or a pharmaceutically acceptable acid addition salt thereof.

2. The pharmaceutical composition defined in claim 1 wherein the fast-acting MAO-B inhibitor contains deprenyl or a pharmaceutically acceptable acid addition salt thereof and the slow-acting inhibitor of a biogenic amine contains deprenyl or a pharmaceutically acceptable acid addition salt thereof.

3. A transdermal pharmaceutical composition for treating a neurodegenerative disease which comprises:

(a) about 1.0 parts by weight of Carbowax 35 000;

(b) about 16.0 parts by weight of Carbowax 4000;

(c) about 53.0 parts by weight of Carbowax 400;

(d) about 2.0 parts by weight of 1,2-propylene-glycol;

(e) about 15.0 parts by weight of xanthan gum;

(f) about 7.0 parts by weight of deprenyl or p-fluorodeprenyl; and (g) about 6.0 parts by weight of glycerine-polyethylene glycol-ricinoleate, said composition being in a liquid crystalline state containing translucent solid crystals of 8 to 10 microns.

* * * * *